(12) United States Patent
Carlsgaard et al.

(10) Patent No.: US 11,864,887 B2
(45) Date of Patent: Jan. 9, 2024

(54) METHOD FOR EMPHASIZING ANALYTE VALUES DURING A THERAPEUTIC WINDOW

(71) Applicant: Roche Diabetes Care, Inc., Indianapolis, IN (US)

(72) Inventors: Eric S. Carlsgaard, Zionsville, IN (US); Nils Babion, Heidelberg (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 201 days.

(21) Appl. No.: 16/342,365

(22) PCT Filed: Oct. 20, 2017

(86) PCT No.: PCT/US2017/057647
§ 371 (c)(1),
(2) Date: Apr. 16, 2019

(87) PCT Pub. No.: WO2018/075922
PCT Pub. Date: Apr. 26, 2018

(65) Prior Publication Data
US 2019/0239780 A1    Aug. 8, 2019

Related U.S. Application Data

(60) Provisional application No. 62/419,054, filed on Nov. 8, 2016, provisional application No. 62/411,001, filed on Oct. 21, 2016.

(51) Int. Cl.
*A61B 5/145* (2006.01)
*A61B 5/00* (2006.01)
(Continued)

(52) U.S. Cl.
CPC ............ *A61B 5/14532* (2013.01); *A61B 5/00* (2013.01); *A61B 5/145* (2013.01); *A61B 5/4836* (2013.01);
(Continued)

(58) Field of Classification Search
CPC ... A61B 5/14532; A61B 5/4836; A61B 5/145; A61B 5/00; A61B 5/6896; A61B 5/7434;
(Continued)

(56) References Cited

U.S. PATENT DOCUMENTS

2003/0114836 A1    6/2003    Estes et al.
2005/0038332 A1    2/2005    Saidara et al.
(Continued)

FOREIGN PATENT DOCUMENTS

CN    105142518 A    12/2015
CN    105324070 A    2/2016
(Continued)

OTHER PUBLICATIONS

Fletcher, Lauren, et al. "Feasibility of an implanted, closed-loop, blood-glucose control device." Immunology 230. (Year: 2001).*
(Continued)

*Primary Examiner* — Patrick Fernandes
(74) *Attorney, Agent, or Firm* — Harness, Dickey & Pierce, P.L.C.

(57) ABSTRACT

In diabetes management applications, recent glucose measurement values may be clinically useful for acute diagnosis and for the calculation of a corrective therapy. However, the physiological significance of these measurements can lessen with time, which can lead to their becoming less relevant for calculating an effective therapy. A technique is presented for emphasizing analyte values in a diabetes management application during a therapeutic window. In this way, a user is notified that the glucose measurement value is the most current measurement and remains usable for therapy applications, such as an insulin bolus calculation.

20 Claims, 6 Drawing Sheets

(51) Int. Cl.
  *G16H 50/30* (2018.01)
  *G16H 20/17* (2018.01)
  *G16H 50/20* (2018.01)
  *G16H 40/63* (2018.01)
  *G16H 20/10* (2018.01)

(52) U.S. Cl.
  CPC .......... *A61B 5/6898* (2013.01); *A61B 5/7435* (2013.01); *G16H 20/17* (2018.01); *G16H 40/63* (2018.01); *G16H 50/20* (2018.01); *G16H 50/30* (2018.01); *A61B 5/0022* (2013.01); *A61B 5/7282* (2013.01); *G16H 20/10* (2018.01)

(58) Field of Classification Search
  CPC .... A61B 5/0022; A61B 5/7282; G16H 50/30; G16H 50/20; G16H 20/17; G16H 20/10; G16H 40/63
  See application file for complete search history.

(56) References Cited

U.S. PATENT DOCUMENTS

| | | | |
|---|---|---|---|
| 2011/0201911 A1* | 8/2011 | Johnson | G06F 3/041 600/365 |
| 2014/0321246 A1 | 10/2014 | Carlsgaard et al. | |
| 2016/0256085 A1 | 9/2016 | Bae et al. | |

FOREIGN PATENT DOCUMENTS

| | | | |
|---|---|---|---|
| CN | 105377118 A | 3/2016 | |
| EP | 2144066 A1 | 1/2010 | |
| EP | 2950101 A1 | 12/2015 | |
| WO | WO-2014145049 A2 * | 9/2014 | ......... A61B 5/14503 |

OTHER PUBLICATIONS

European Search Report issued in EP 17862472.2, dated Apr. 14, 2020.
International Search Report and Written Opinion of the International Searching Authority issued in PCT/US2017/057647, dated Jan. 4, 2018; ISA/US.

\* cited by examiner

METHOD FOR EMPHASIZING ANALYTE VALUES DURING A THERAPEUTIC WINDOW

CROSS-REFERENCE TO RELATED APPLICATIONS

This application is a U.S. National Phase Application under 35 U.S.C. 371 of International Application No. PCT/US2017/057647 filed on Oct. 20, 2017, which claims the benefit of U.S. Provisional Application Nos. 62/411,001, filed on Oct. 21, 2016 and 62/419,054, filed on Nov. 8, 2016. The entire disclosures of the above applications are incorporated

FIELD

The present disclosure relates generally to a method for emphasizing analyte values in a diabetes management application during a therapeutic window.

BACKGROUND

Diabetes management devices may receive, store, and display analyte data collected from a diagnostic measurement device. A plurality of measurements may be displayed on these devices to remind the user of historical readings or to notify the user of significant trends. In some cases, the most recent measurement values may be clinically useful for acute diagnosis and for the calculation of a corrective therapy. However, the physiological significance of these measurements can lessen with time, which can lead to their becoming less relevant for calculating an effective therapy. Thus, there is a need to exhibit the significance of such readings to the user in order to unintentionally avoid missing a therapeutic window.

This section provides background information related to the present disclosure which is not necessarily prior art.

SUMMARY

This section provides a general summary of the disclosure, and is not a comprehensive disclosure of its full scope or all of its features.

A computer-implemented method is presented for displaying glucose measurements by a diabetes management application residing on a computing device. The method includes: receiving a current glucose measurement for a subject, where the current glucose measurement has an associated timestamp; determining a therapeutic window of time (e.g., 15 minute) in which the current glucose measurement is usable in a therapy calculation; displaying the current glucose measurement on a result screen, where the current glucose measurement is presented prominently in relation to other text on the result screen while the timestamp associated with the current glucose measurement falls within the therapeutic window of time; and displaying the current glucose measurement on a result screen without prominence in relation to other text on the result screen after therapeutic window of time expires. For example, the current glucose measurement may be displayed prominently by changing one or more of color, shape, size or font (e.g. bold) of alphanumeric characters indicative of the current glucose measurement.

After the expiration of the therapeutic window, an indication that the therapeutic window has expired may be displayed on the result screen. The method may further include: navigating from the result screen to another screen in the diabetes management application and continuing to present the current glucose measurement prominently on the another screen in relation to other text on the another screen so long as the timestamp associated with the current glucose measurement falls within the therapeutic window of time. Additionally, an amount of insulin to administer to the subject is computed using the current glucose measure only while the timestamp associated with the current glucose measurement falls within the therapeutic window of time.

In one embodiment, an indicia of the therapeutic window of time is displayed on the result screen concurrently with the prominently displayed current glucose measurement.

In another embodiment, a countdown of the therapeutic window of time is displayed on the result screen concurrently with the prominently displayed current glucose measurement.

Further areas of applicability will become apparent from the description provided herein. The description and specific examples in this summary are intended for purposes of illustration only and are not intended to limit the scope of the present disclosure.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

Figure 1:
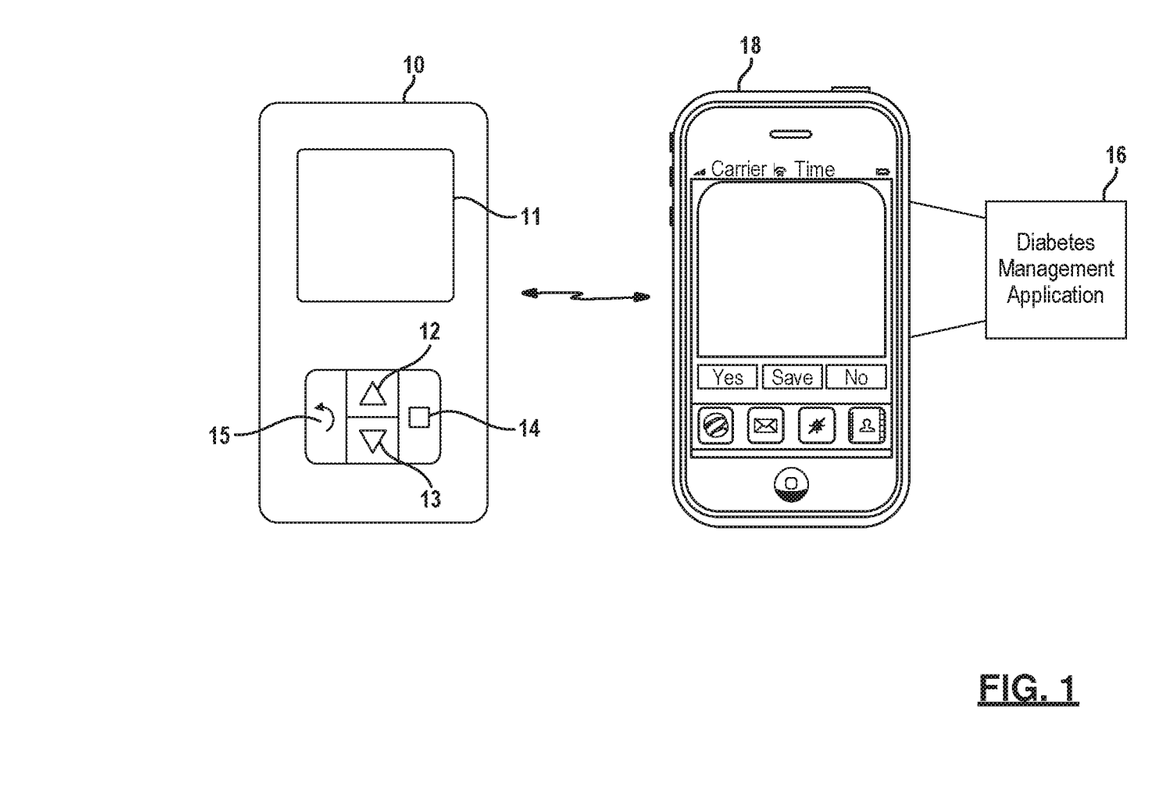
FIG. 1 is a diagram depicting a handheld glucose meter in data communication with a diabetes management application residing on a mobile phone.

FIG. 1 depicts an example handheld glucose meter 10. The handheld glucose meter 10 includes a display 11 and various buttons that can be used to control the handheld glucose meter 10. The buttons may include an up button 12, a down button 13, a select button 14 and a back button 15. The up button 12 and the down button 13 may be used to scroll up and down a screen being displayed on the display 11. The select button 14 may be used to make a selection, such as to press 'OK' or to click on an option being displayed on the display 11. The back button 15 may be used to navigate back to a previous screen being displayed on the handheld glucose meter 10.

In this example embodiment, the handheld glucose meter 10 is in data communication via a wireless data link with a diabetes management application 16. The handheld glucose meter 10 is configured to receive a sample of blood from a patient and determine a blood glucose measure for the patient from the blood sample. One or more blood glucose measurements may in turn be transmitted over the wireless data link to the diabetes management application 16 for further processing. In an example embodiment, the diabetes management application 16 resides on a mobile phone 18. In other embodiments, the diabetes management application 16 may be native to a remote server with its user interface presented on the mobile phone 18. In some embodiments, data is transferred to and from the handheld glucose meter 10 using the Bluetooth wireless technology standard (e.g., low energy feature of Bluetooth 4.0) although other types of communication transports are contemplated by this disclosure, such as Wi-Fi, ZigBee, NFC (Near Field Communications), or the like.

Figure 2:
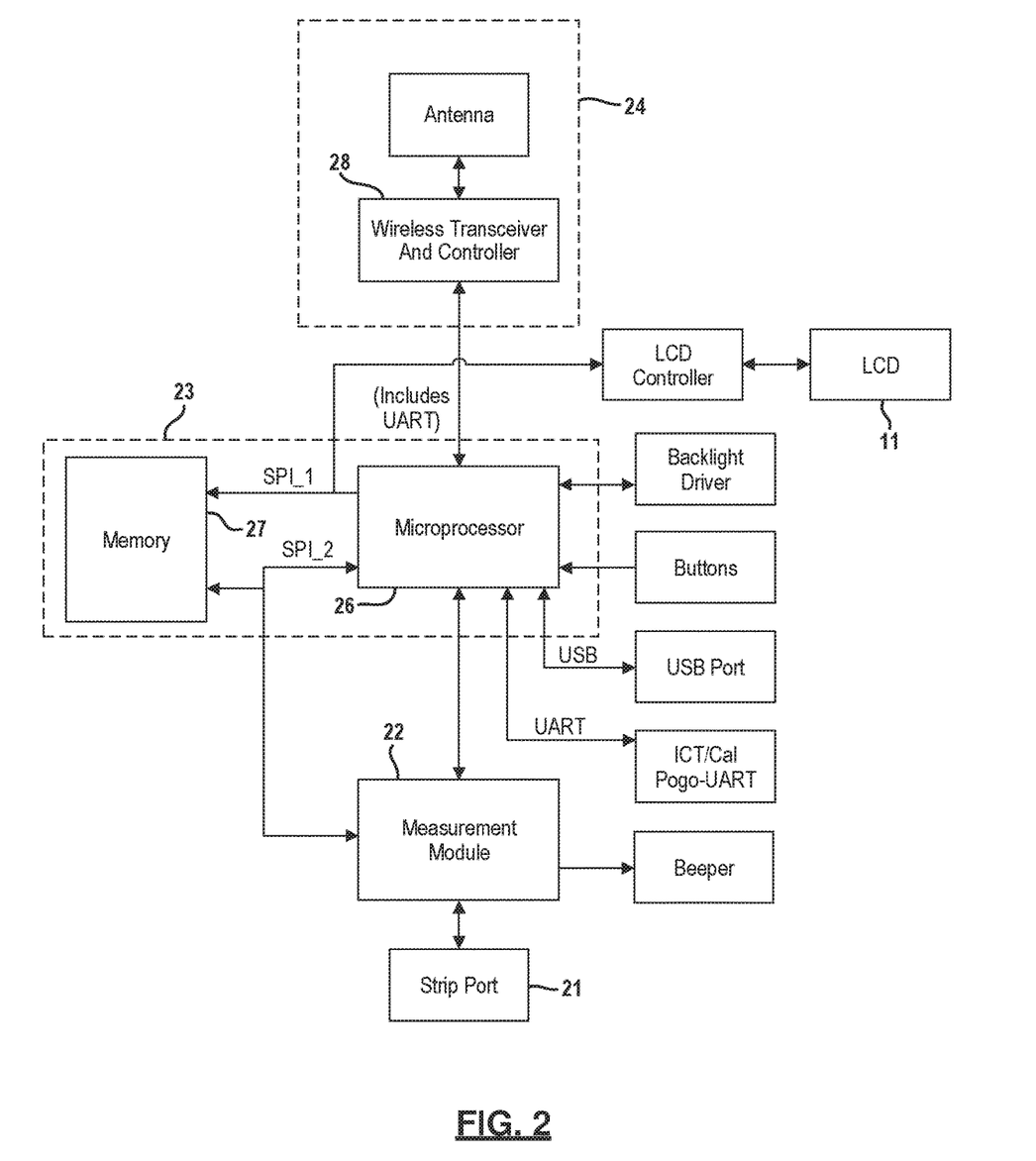
FIG. 2 is a block diagram of an example hardware arrangement for the handheld glucose meter.

FIG. 2 depicts an example hardware arrangement for the handheld glucose meter 10. The handheld glucose meter 10 is comprised generally of a measurement module 22, a processing subsystem 23 and a communication subsystem 24. Each of these components is further described below. While the primary components are discussed herein, it is understood that other components (e.g., batteries) may be needed for the overall operational of the meter.

The measurement module 22 cooperatively interacts with a test strip inserted into a strip port 21 to determine a glucose measurement from the sample of blood place on a reaction site of the test strip. The measurement module 22 may include a code key that includes calibration information for the test strips being read by the meter. As used herein, the term module may refer to, be part of, or include an application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above. The term module may further include memory that stores code executed by the processor, where code, as used above, may include software, firmware, and/or microcode, and may refer to programs, routines, functions, classes, and/or objects.

The processing subsystem 23 is configured to receive the glucose measurements from the measurement module 22 which may in turn be stored by the processing subsystem 23. Glucose measurements may also be displayed by a UI manager of the processing subsystem 23 on the display 11. The user can interact with the meter using various user interface components, such as buttons, switches, a speaker, a microphone, USB port, etc. Each of these components is interfaced with the processing subsystem 23. In an exemplary embodiment, the processing subsystem 23 includes a microprocessor 26 and one or more volatile and/or nonvolatile memories 27 although other implementations are envisioned for the processing subsystem.

The processing subsystem 23 is also interfaced with the communication subsystem 24. In an exemplary embodiment, the communication subsystem 24 includes a wireless transceiver 28. The wireless transceiver 28 operates to communicate the glucose measurements and other data wirelessly via a data link to a remote device physically separated from the meter. The communication subsystem 24 can also include an antenna, microcontroller, voltage and power control circuits and a flash memory device. Although a few primary components of the handheld glucose meter 10 are discussed herein, it is readily understood that other components (e.g., power source) may be needed to implement the meter.

Figure 3:
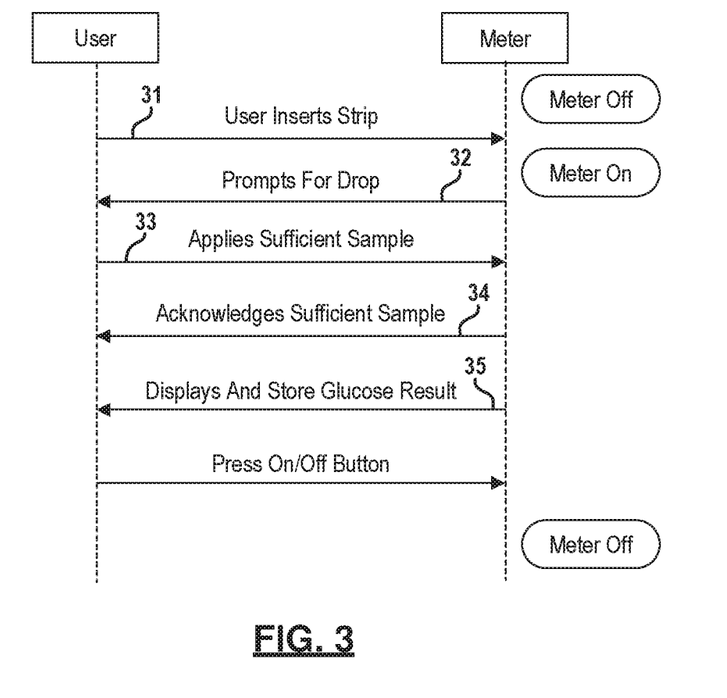
FIG. 3 is a sequence diagram illustrating an exemplary sequence for taking a blood glucose measure using the glucose meter.

FIG. 3 depicts an exemplary sequence for taking a blood glucose measure using the glucose meter 10. The user may insert a test strip at 31 into a port of the glucose meter 10. Insertion of the test strip prompts the glucose meter to power on. The user may alternatively power on the glucose meter using an on/off button. In this case, the glucose meter will prompt the user to insert a test strip. The user may also power on the glucose meter without having inserted a test strip into the meter. In any of these cases, the glucose meter may perform a quality check on the test strip inserted into the meter. Once the quality check has been completed, the meter is ready to perform a test.

To begin a test, the user is prompted at 32 for a sample of blood. In response to the prompt, the user provides a blood sample at 33 using the test strip, where the test strip includes a reaction site that receives the blood sample from the patient. Upon receipt of the blood sample, the glucose meter 10 will proceed to analyze the blood sample in a manner readily known in the art. Before doing so, the glucose meter may acknowledge the sufficiency of the blood as indicated at 34.

During the analysis, a blood glucose measure is obtained from the blood sample. The blood glucose measure will be displayed to the user and stored on the glucose meter as indicated at 35. In one embodiment, the glucose measurement may be displayed by a diabetes management application residing on the glucose meter 10. The current glucose measurement may be displayed on a result screen immediately after the measurement is taken. Alternatively, user input such as navigating from a home screen to the result screen may be required to display the current blood glucose measurement. In either case, the current glucose measurement is displayed on the result screen in the manner further described below. It is envisioned that stored glucose measures may be uploaded subsequently in a batch manner from the glucose meter to a physician's computer.

Figure 4:
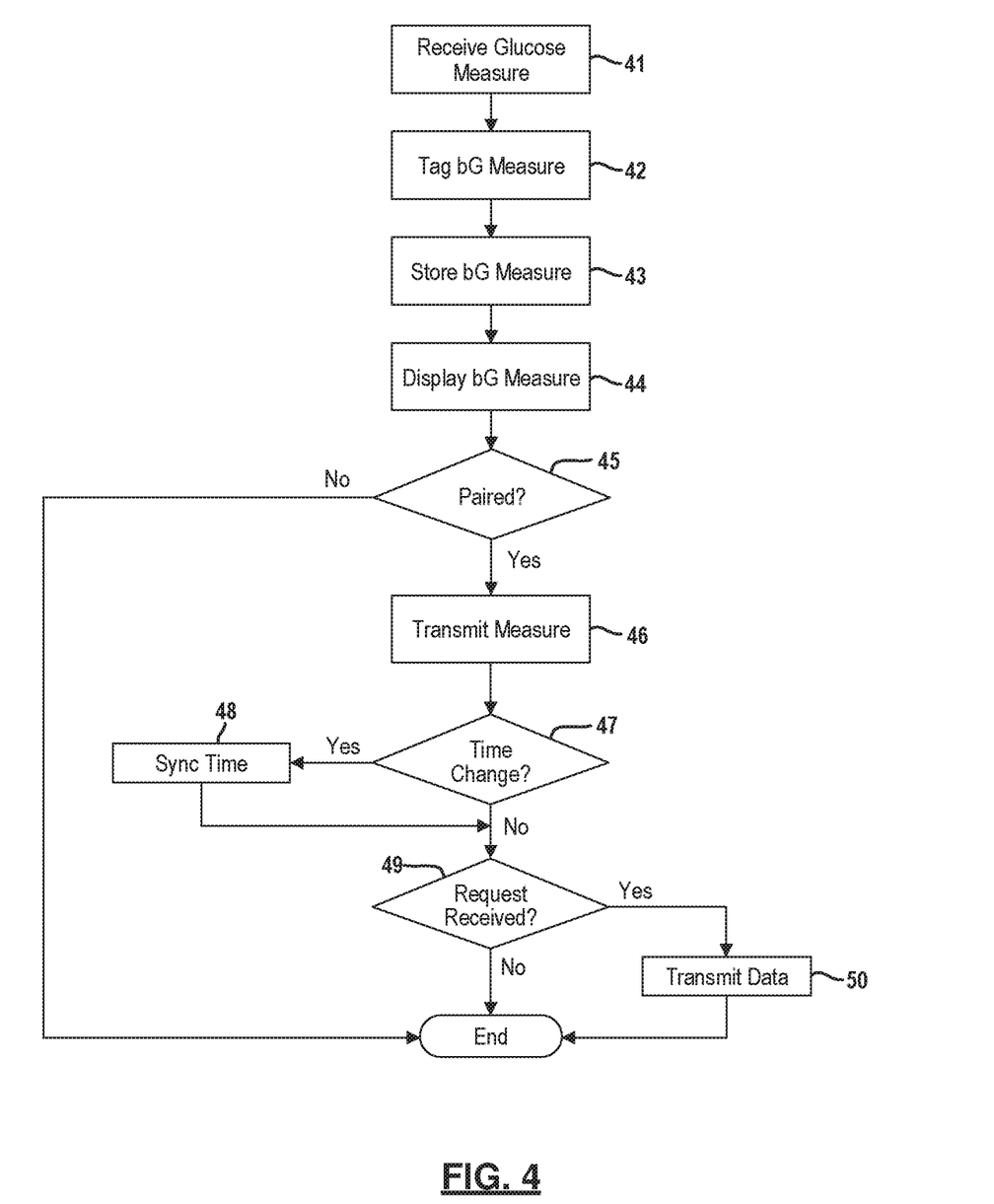
FIG. 4 is a flowchart illustrating an exemplary technique for transmitting blood glucose measures individually from the glucose meter.

Rather than sending blood glucose measures in a batch manner, the glucose meter 10 may be configured to transmit blood glucose measures individually as shown in FIG. 4. The blood glucose measures may be transmitted, for example to a mobile phone or some other portable computing device carried by the user. Because the mobile phone is typically in close proximity to the user, it may be used as a data collector for the patient's blood glucose measures. A diabetes management application 16 residing on the mobile phone 18 can then be used for data analysis as well as other sophisticated diabetes management functions. Consequently, the processing power and memory available on the glucose meter can be streamlined, thereby reducing the cost of the glucose meter 12.

Upon determining a blood glucose measure, the blood glucose measure is first tagged at 42 with identifying information. Identifying information may include but is not limited to a name of the patient to which the measure pertains to, a timestamp for when the measure was taken, a serial number for the meter and other information pertaining to the test strip. Of note, each blood glucose measure is also tagged with a unique sequence number assigned by the glucose meter. In one embodiment, a counter is incremented each time a glucose measure is taken and the value of the counter is assigned to the blood glucose measure. The sequence number may be used to retrieve missing data from the glucose meter as is further described below. Once tagged, the blood glucose measure is stored at 43 in a memory of the glucose meter and displayed to the user at 44 on a display of the glucose meter.

Next, the glucose meter determines at 45 whether it is paired via a wireless data link with another device, such as mobile phone 18. The current blood glucose measure is transmitted at 46 to the mobile phone when the glucose meter is paired to the mobile phone. In one embodiment, the blood glucose measure is transmitted automatically and without user intervention. In another embodiment, the blood glucose measure is transmitted automatically in response to the user navigating away from the measurement result screen. It is envisioned that the mobile phone 18 and/or the diabetes management application 16 is authenticated with the glucose meter 10 during the pairing process.

In addition to transmitting the blood glucose measure, the glucose meter 10 can synchronize its time with the mobile phone 18. During initial setup or thereafter, the glucose meter 10 may be configured by the user to synchronize its clock with the mobile phone 18. By enabling this time synchronization feature, the user is designating the mobile phone 18 as the master device. Current time on the mobile phone is transmitted to the glucose meter during each data exchange. Because a user is interacting frequently with their mobile phone, the time reported by the mobile phone is likely to be accurate. The glucose meter will compare the current time on the mobile phone to the current time maintained by the glucose meter as indicated at 47. If the time synchronization feature has been enabled by the user and the difference between the two clocks exceeds a variance (e.g., 2 minutes), the glucose meter will set its clock to the current time of the mobile phone as indicated at 48. Conversely, the glucose meter may retain its current time if time synchronization feature has not been enabled or the difference between the two clocks is less than the variance threshold. In an alternative embodiment, the glucose meter will set its clock to the current time of the mobile phone if the difference between the two clocks is less than the variance threshold and the time synchronization feature is enabled. It is envisioned that other parameters, such as date/time format, target glucose ranges, hypo waning levels, etc., can also be synchronized between the two devices.

During each data exchange, the glucose meter 10 may also receive a request for missing glucose measures at 49 from the diabetes management application 16. In one embodiment, the request identifies any missing glucose measures by its sequence number as will be further described below. In response to receiving a request, the glucose meter 10 will transmit the missing glucose measures at 50 to the diabetes management application 16. It is to be understood that only the relevant steps are discussed in relation to FIG. 4 but that other software-implemented instructions may be needed to transmit data from the glucose meter.

Figure 5:
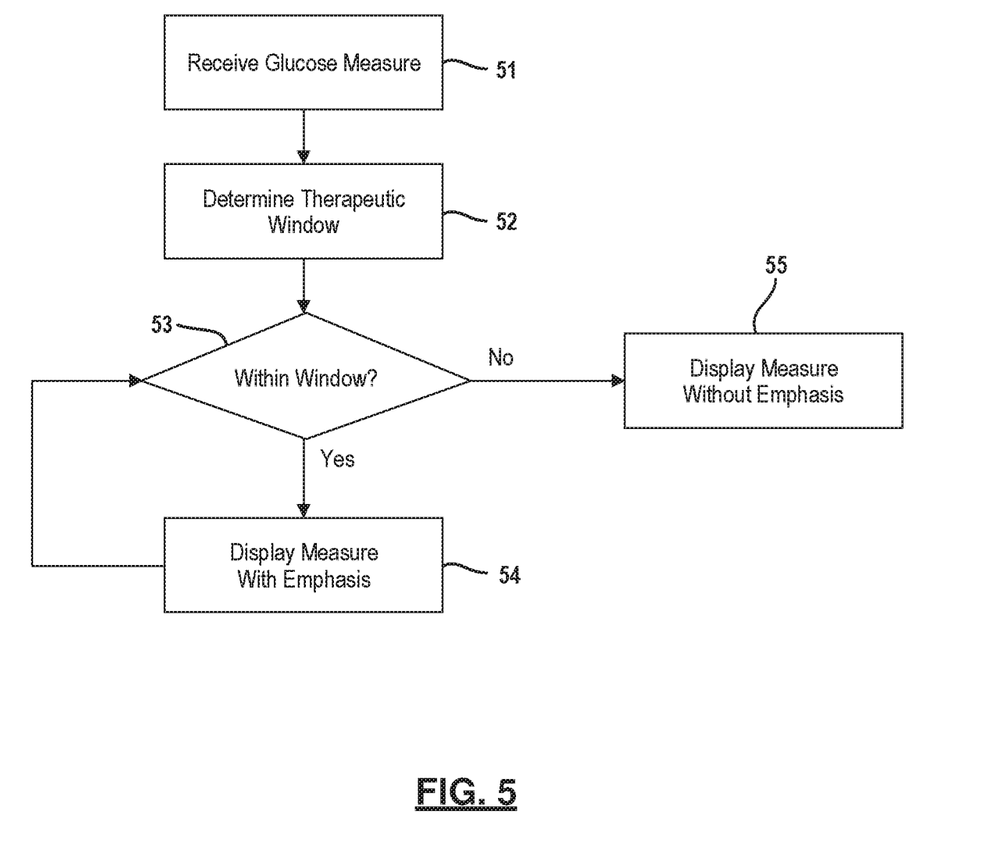
FIG. 5 is a flowchart illustrating an example method for displaying glucose measurements on a result screen.

FIG. 5 depicts an exemplary method for displaying glucose measures by the diabetes management application 16 residing on the mobile phone 18. In the exemplary embodiment, glucose measures are transmitted individually to the diabetes management application 16 as described in relation to FIG. 4. It is envisioned that other techniques for transmitting the glucose measures to the diabetes management application 16 are contemplated by this disclosure. The diabetes management application in turn processes the glucose measures, for example as described below. In one embodiment, the diabetes management application is software executed by a computer processor residing on the mobile phone 18. It is understood that that diabetes management application may take other forms and be implemented on other types of computing device, such as watches, tablets, laptops and the like.

Upon receiving a glucose measure, the glucose measure is stored in a local data store commonly referred to as a logbook. In an example embodiment, the current glucose measurement is displayed on a result screen of the mobile phone upon receipt by the diabetes management application. In other embodiments, the current glucose measurement is displayed once a user navigates to the result screen of the diabetes management application. Format of the current glucose measurement depends upon the timing at which the display occurs in relation to a therapeutic window as further described below.

A therapeutic window of time for the current glucose measurement is determined at 54. The current glucose measurement is clinically useful for diagnosing patient conditions and determining corrective actions. On the other hand, the physiological significance of a measurement can lessen with time.

Therefore, it is desirable that a therapy calculation for treating a patient's condition be computed in a clinically useful period of time after the measurement was taken, i.e., a therapeutic window of time in which a glucose measurement is usable in a therapy calculation. Medical studies have shown that the therapeutic window is preferably a period of time in the range of 15 to 30 minutes. For example, it is rare for blood glucose to change at a rate outside of [−2 mg/dl/min, 2 mg/dl/min], so the change in the value of blood glucose after a 15 minute delay is likely to be in the range BG+/−30 mg/dl which spans a range of 60 mg/dl. A typical glucose target range spans the range from 80-140 mg/dl. Because the range of 60 mg/dl is less than the target range, a correction within a 15 therapeutic window is still likely to fall into the target range. In a review of at least one course of CGM data, only about 6% of data values were outside the +/−30 mg/dl range after 15 minutes. Conversely, therapy calculations made outside the therapeutic window are considerably less accurate than those made inside the therapeutic window and consequently are less effective at treating the patient's condition. Techniques described in this disclosure are intended to highlight this relationship and thereby influence user behavior.

In one embodiment, each glucose measurement has an associated timestamp indicating when the measurement was taken. The therapeutic window for the current glucose measurement can be determined using the associated timestamp. For example, if the current measurement was taken at 2:05 pm, then the therapeutic window is defined as being 2:05 pm to 2:20 pm. In another embodiment, a countdown timer defines the therapeutic window and is started when the glucose measurement is taken by or received from the glucose meter. Other techniques for defining a therapeutic window are also contemplated by this disclosure.

To determine whether the current glucose measurement falls within the therapeutic window, the current time is then compared at 53 to the therapeutic window. If the current time falls within the therapeutic window, then the current glucose measurement is presented on a result screen prominently in relation to other text on the result screen. For example, the current glucose measurement can be emphasized by changing one or more of the color, shape, size, or font (e.g., bold, italicize, etc.) of the alphanumeric characters indicative of the current glucose measurement. In this way, the user is notified that the glucose value is the most current measurement and remains usable for therapy applications, such as an insulin bolus calculation.

Figure 6A:
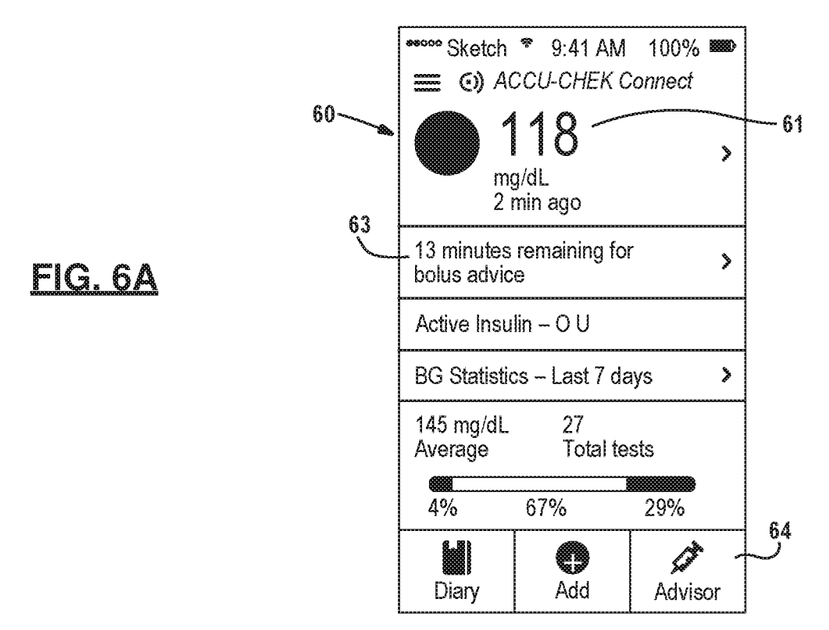
FIGS. 6A and 6B are screenshots of example screens employed by the diabetes management application.

FIG. 6A depicts an example result screen 60 used by the diabetes management application. In this example embodiment, the value 61 for the current glucose measurement (i.e., 118) is enlarged and bolded to indicate that it's the most current measure and remains usable within the therapeutic window. Indicia of the therapeutic window may also be displayed concurrently with the current glucose measurement. For example, the start time and end time of the window (e.g., the therapeutic window for the current glucose measurement is 2:05-2:20 pm) may be displayed on the result screen. In another example, a countdown of the therapeutic window (e.g., 13 minutes remaining for bolus advice) may be displayed as indicated at 63 in FIG. 6A. In yet another example, the duration of the therapeutic window may be given in conjunction with (or without) the countdown value. In any case, this feature helps to warn the user about the expiring eligibility of the glucose measurement.

Figure 6B:
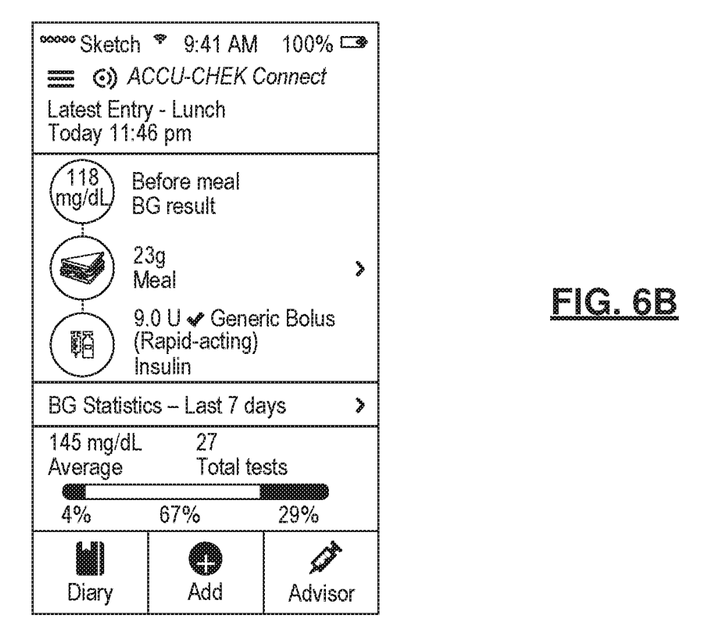

In one embodiment, the user may navigate from the result screen to the home screen seen in FIG. 6B, where the home screen show the most recent glucose measure. While the therapeutic window remains active, the current glucose measurement may continue to be enlarged and bolded on the home screen, thereby indicating it remains usable for therapy applications. Once the therapeutic window expires, the current glucose measurement is de-emphasized. Note the un-bolded, reduced size of the font. Alternatively, the current glucose measurement may be de-emphasized once user navigates away from the result screen. In this example, the home screen also show the meal carbs eaten as well as an amount of insulin administered.

In some embodiments, the result screen 60 may include an advisor button 64 for navigating to a bolus advisor or bolus calculation function. In the event the user actuates the advisor button while the therapeutic window remains active, a bolus calculation (i.e., amount of insulin to be administered) is performed using the current glucose measurement. In the event the user actuates the advisor button after the therapeutic window expires, the bolus calculation may not be performed or may be performed with the results including certain qualifiers (e.g., insulin recommendation is based on stale glucose measures). A bolus calculation is merely an example of a therapy calculation that can be performed using the current glucose measurement. In some embodiment, the advisor button is enabled during the therapeutic window but disabled outside of the therapeutic window (e.g., gray out). It is envisioned that other features may be enabled and/or disabled depending on whether the current time falls within the therapeutic window Returning to FIG. 5, once the therapeutic window expires, the current glucose measurement is de-emphasized as indicated at 55. The current glucose measurement can be de-emphasized by removing any changes made to the alpha-numeric characters representing the glucose measurement. For example, bolded numbers can be un-bolded or an enlarged font size can be returned to its normal font size. In addition, an indication that the therapeutic window has expired may be presented on the display in response to the expiration of the therapeutic window. This concept can be used to highlight analyte values even when bolus advice is not activated to train users to be more diligent and complete with entering additional contextual information with each measurement value. This concept is also not limited to glucose measurement values and could be applied to other types of data collected on diabetes management devices (e.g. exercise, food intake, health state) that may be therapeutically significant.

Furthermore, this concept could be applied to non-discrete measurement values (e.g. continuous glucose monitors or continuous physiological monitoring in general) that may be therapeutically significant. For example, the user may benefit from emphasizing a discrete CGM value which can be used to calculate bolus advice over all of the other values collected during a similar time period. It is to be understood that only the relevant steps are discussed in relation to FIG. 5 but that other software-implemented instructions may be performed by the diabetes management application. It is also understood that this method for displaying glucose measurements may be implemented by a diabetes management application residing on a glucose meter.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A computer-implemented method for displaying glucose measurements by a diabetes management application residing on a computing device, comprising:
   receiving, by the diabetes management application, a current glucose measurement for a subject, where the current glucose measurement has an associated timestamp;
   determining, by the diabetes management application, a therapeutic window of time in which the current glucose measurement is usable in a therapy calculation;
   displaying, by the diabetes management application, the current glucose measurement on a result screen, where the current glucose measurement is presented prominently in relation to other text on the result screen while current time is within the therapeutic window of time;
   displaying an indicia of the therapeutic window of time on the result screen concurrently with the prominently displayed current glucose measurement;
   displaying, by the diabetes management application, the current glucose measurement on a result screen without prominence in relation to other text on the result screen after therapeutic window of time expires; and
   displaying, by the diabetes management application, an advisor button on the result screen for navigating to a therapy advisor or therapy calculation function, where the advisor button is enabled while current time is within the therapeutic window of time and disabled after therapeutic window of time expires.

2. The method of claim 1 wherein displaying the current glucose measurement prominently by changing one or more of color, shape, size or font of alphanumeric characters indicative of the current glucose measurement.

3. The method of claim 1 wherein displaying the current glucose measurement prominently by balding the font of the alphanumeric characters indicating the current glucose measurement.

4. The method of claim 1 further comprises displaying a countdown of the therapeutic window of time on the result screen concurrently with the prominently displayed current glucose measurement.

5. The method of claim 1 wherein the therapeutic window of time is fifteen minutes.

6. The method of claim 1 further comprises displaying an indication that the therapeutic window has expired on the result screen in response to the expiration of the therapeutic window.

7. The method of claim 1 further comprise navigating from the result screen to another screen in the diabetes management application and continuing to present the current glucose measurement prominently on the another screen in relation to other text on the another screen so long as the associated timestamp associated with the current glucose measurement falls within the therapeutic window of time.

8. The method of claim 1 further comprises computing an amount of insulin to administer to the subject using the current glucose measure only while the associated timestamp associated with the current glucose measurement falls within the therapeutic window of time.

9. A computer-implemented method for displaying glucose measurements by a diabetes management application residing on a computing device, comprising:
   receiving, by the diabetes management application, a current glucose measurement for a subject, where the current glucose measurement has an associated timestamp;
   determining, by the diabetes management application, a therapeutic window of time in which the current glucose measurement is usable in a therapy calculation;
   comparing, by the diabetes management application, current time with a therapeutic window of time, where the therapeutic window of time indicates when the current glucose measurement is usable in a therapy calculation;
   displaying, by the diabetes management application, the current glucose measurement prominently on a result screen in response to the associated timestamp associated with the current glucose measurement falling in the therapeutic window of time;
   displaying, by the diabetes management application, the current glucose measurement on a result screen without prominence in relation to other text on the result screen in response to the timestamp associated with the current glucose measurement falling outside the therapeutic window of time; and
   displaying, by the diabetes management application, an advisor button on the result screen for navigating to a therapy advisor or therapy calculation function, where the advisor button is enabled in response to the associated timestamp associated with the current glucose measurement falling in the therapeutic window of time and disabled in response to the timestamp associated with the current glucose measurement falling outside the therapeutic window of time.

10. The method of claim 9 wherein displaying the current glucose measurement prominently by changing one or more of color, shape, size or font of alphanumeric characters indicative of the current glucose measurement.

11. The method of claim 9 wherein displaying the current glucose measurement prominently by balding the font of the alphanumeric characters indicating the current glucose measurement.

12. The method of clam 9 further comprises displaying an indicia of the therapeutic window of time on the result screen concurrently with the prominently displayed current glucose measurement.

13. The method of claim 9 further comprises displaying a countdown of the therapeutic window of time on the result screen concurrently with the prominently displayed current glucose measurement.

14. The method of claim 9 further comprise navigating from the result screen to another screen in the diabetes management application and continuing to present the current glucose measurement prominently on the another screen in relation to other text on the another screen so long as the associated timestamp associated with the current glucose measurement falls within the therapeutic window of time.

15. The method of claim 9 further comprises computing an amount of insulin to administer to the subject using the current glucose measure only while the associated timestamp associated with the current glucose measurement falls within the therapeutic window of time.

16. A system for managing diabetes care, comprising:
   a handheld glucose meter configured to determine a current glucose measurement for a subject, such that the current glucose measurement has an associated timestamp, and operable to transmit the current glucose measurement via a wireless communication link, wherein the determination is made from a test strip inserted in a port of the handheld glucose meter and the test strip has a reaction site for receiving a sample of fluid from the subject; and a diabetes management application residing on a portable computing device and configured to receive the current glucose measurement via the wireless communication link from the handheld glucose meter, wherein the diabetes management application determines a therapeutic window of time in which the current glucose measurement is usable in a therapy calculation, presents the glucose measurement prominently in relation to other text on a display of the portable computing device while current time falls within the therapeutic window of time and presents glucose measurement on the display without prominence in relation to other text on the display after therapeutic window of time expires;

wherein the diabetes management application displays an advisor button on the result screen for navigating to a therapy advisor or therapy calculation function, such that the advisor button is enabled while current time is within the therapeutic window of time and disabled after therapeutic window of time expires.

17. The system of claim 16 wherein diabetes management application displays the glucose measurement prominently by changing one or more of color, shape, size or font of alphanumeric characters indicative of the current glucose measurement.

18. The system of claim 16 wherein diabetes management application displays an indicia of the therapeutic window of time on the display concurrently with the prominently displayed glucose measurement.

19. The system of claim 16 wherein diabetes management application displays a countdown of the therapeutic window of time on the display concurrently with the prominently displayed current glucose measurement.

20. The system of claim 16 wherein the handheld glucose meter includes
- a housing with a port for receiving a test strip, where the test strip has a reaction site for receiving a sample of fluid from a patient;
- a measurement module residing in the housing and operable with the test strip to measure glucose in a sample of fluid residing on the test strip; and
- a display integrated into the housing.

* * * * *